US00PP26148P3

(12) United States Plant Patent
Danziger

(10) Patent No.: US PP26,148 P3
(45) Date of Patent: Nov. 24, 2015

(54) ***PETUNIA* PLANT NAMED 'DLITT299'**

(50) Latin Name: *Petunia sensu wijsman*
Varietal Denomination: DLITT299

(71) Applicant: Gavriel Danziger, Moshav Mishmar Hashiva (IL)

(72) Inventor: Gavriel Danziger, Moshav Mishmar Hashiva (IL)

(73) Assignee: Danziger "DAN" Flower Farm (IL)

( * ) Notice: Subject to any disclaimer, the term of this patent is extended or adjusted under 35 U.S.C. 154(b) by 31 days.

(21) Appl. No.: 13/986,304

(22) Filed: Apr. 19, 2013

(65) Prior Publication Data

US 2014/0317812 P1 Oct. 23, 2014

(51) Int. Cl.
*A01H 5/02* (2006.01)

(52) U.S. Cl.
USPC ..... Plt./356.18
CPC ..... *A01H 5/02* (2013.01)

(58) Field of Classification Search
USPC ..... Plt./356.18
CPC ..... A01H 5/02; A01H 5/00
See application file for complete search history.

(56) References Cited

PUBLICATIONS

"Plants with restricted propagation", May 2014.*
Greenhouse Grower, Jul. 2012.*

* cited by examiner

*Primary Examiner* — Keith O. Robinson
(74) *Attorney, Agent, or Firm* — Cassandra Bright

(57) ABSTRACT

A new and distinct *Petunia* cultivar named 'DLITT299' is disclosed, characterized by small, very dark purple flowers with greenish-yellow stripes, triangles or dots around the margin. The new variety is of medium vigor and moderately well branched as well as abundant in flowering and of mounded shape. The new variety is a *Petunia,* normally produced as an outdoor garden or container plant.

2 Drawing Sheets

Figure 1:
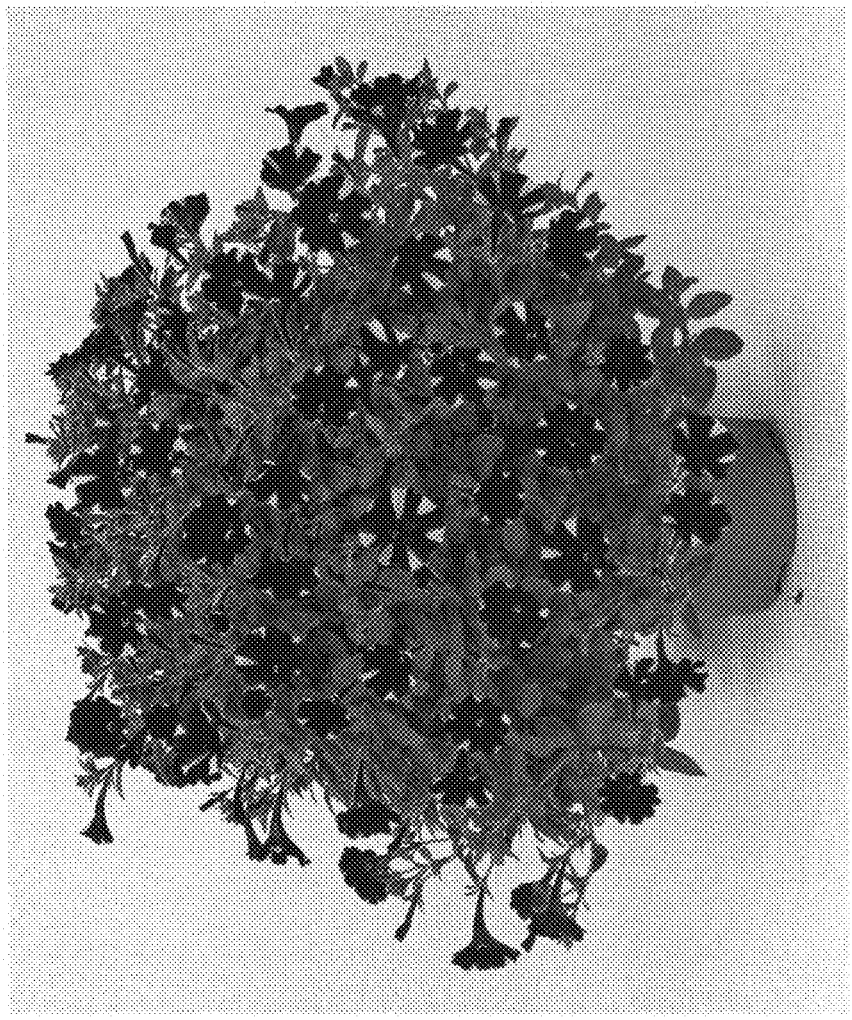

Latin name of the genus and species: *Petunia sensu wijsman.*

Variety denomination: 'DLITT299'.

BACKGROUND OF THE INVENTION

The new *Petunia* cultivar is a product of a planned breeding program conducted by the inventor, Gavriel Danziger, in Moshav Mishmar Hashiva, Israel. The objective of the breeding program was to produce new *Petunia* varieties for ornamental commercial applications. The cross resulting in this new variety was made during March of 2011.

The seed parent is the unpatented non-commercial seedling variety referred to as *Petunia* '8-2651'. The pollen parent is the unpatented seedling variety referred to as *Petunia* '10-4179', containing the black gene described in utility patent U.S. Pat. No. 7,642,436. The new variety was discovered in September of 2011 by the inventor in a group of seedlings resulting from the 2011 crossing, in a research greenhouse in Moshav Mishmar Hashiva, Israel.

Asexual reproduction of the new cultivar has been performed by vegetative cuttings. This was first performed at a research greenhouse in Moshav Mishmar Hashiva, Israel in October of 2011 and has shown that the unique features of this cultivar are stable and reproduced true to type in more than 25 generations.

SUMMARY OF THE INVENTION

The cultivar 'DLITT299' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DLITT299' These characteristics in combination distinguish 'DLITT299' as a new and distinct *Petunia* cultivar:

1. Mounded plant shape.
2. Moderate branching.
3. Flower color is very dark purple with greenish-yellow stripes, triangles or dots around the margin.
4. Flower size is small.
5. Abundant flowering.
6. Medium vigor.

Plants of the new cultivar 'DLITT299' are similar to plants of the seed parent, *Petunia* '8-2651' in most horticultural characteristics, however, plants of the new cultivar 'DLITT299' are smaller, and less branched than the seed parent. 'DLITT299' also produces an abundant quantity of very dark purple flowers with greenish-yellow stripes, triangles or dots around the margin, compared to the medium quantity of medium size blue flowers with the white rim of the seed parent. Additionally 'DLITT299' produces a mounded plant habit compared to the semi upright plant habit of the seed parent '8-2651'.

Plants of the new cultivar 'DLITT299' are similar to plants of the pollen parent; *Petunia* '10-4179' in most horticultural characteristics, however, plants of the new cultivar 'DLITT299' produce an abundant quantity of small very dark purple flowers with greenish-yellow stripes, triangles or dots around the margin compared to the medium quantity of large, dark purple flowers with white stripes of the seed parent.

Additionally 'DLITT299' produces a mounded plant habit compared to the trailing plant habit of '10-4179'.

COMMERCIAL COMPARISON

Plants of the new cultivar 'DLITT299' are comparable to the variety *Petunia* 'Balpephan' U.S. Plant Pat. No. 22,440. The two *Petunia* varieties are similar in most horticultural characteristics; however, the new variety 'DLITT299' differs in producing smaller, very dark purple flowers with greenish-yellow stripes, triangles or dots around the margin compared to the purple flowers with wide yellow stripes of the comparator 'Balpephan'. Additionally 'DLITT299' produces leaves of small size whereas leaves of comparator 'Balpephan' are of medium size. Plants of 'DLITT299' produce flowers with a flat interior aspect compared to the curved, rolled inside of flowers of comparator 'Balpephan'.

Plants of the new cultivar 'DLITT299' can also be compared to the commercial variety *Petunia* 'Balpepin' U.S. Plant Pat. No. 22,414. These varieties are similar in most horticultural characteristics, however 'DLITT299' produces smaller very dark purple flowers with greenish-yellow stripes, triangles or dots around the margin compared to the larger purple flowers with yellow-white stripes of comparator 'Balpepin'. Foliage of 'DLITT299' is narrow compared to the wide leaves of comparator 'Balpepin'. Additionally 'DLITT299' produces a mounded plant form of medium vigor compared to the vigorous, semi-upright form of comparator 'Balpepin'.

BRIEF DESCRIPTION OF THE PHOTOGRAPHS

The accompanying photograph in FIG. 1 illustrates in full color a typical plant of 'DLITT299' grown in a greenhouse, in a 13 cm pot. Age of the plant photographed is approximately 3 months from a rooted cutting.

Figure 2:
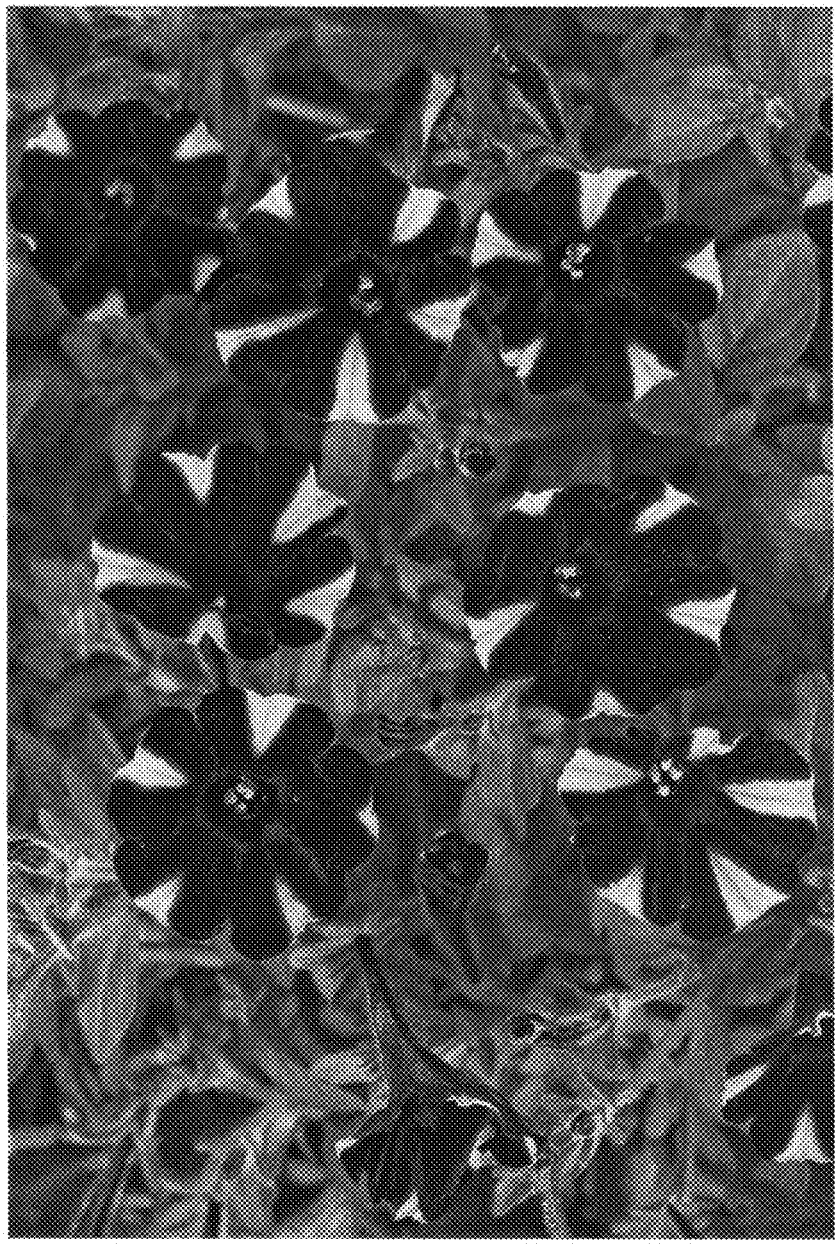

FIG. 2 illustrates in full color a close up of a typical bloom of 'DLITT299'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DLITT299' plants grown outdoors during, Spring, Summer, and Autumn in Moshav Mishmar Hashiva, Israel. The growing temperature ranged from 20° C. to 35° C. during the day and from 17° C. to 23° C. during the night. General light conditions are bright, normal sunlight. Measurements and numerical values represent averages of typical plant types.

Botanical classification: *Petunia sensu wijsman* 'DLITT299'.

PROPAGATION

Time to initiate roots: About 10 to 14 days.
Root description: Fibrous.

PLANT

Age of plant described: Approximately 60 days from rooted cutting.
Pot size of plant described: 13 cm.
Growth habit: Mounded.
Height: To top of flowers about 20 cm.
Plant spread: 60 cm.
Growth rate: Medium.
Branching characteristics: Moderately branched.
Quantity of primary lateral branches: 6.
Characteristics of primary lateral branches:
- *Form.*—Cylindrical.
- *Length.*—25 cm.
- *Diameter.*—About 0.3 cm.
- *Color.*—Yellow-green group 144B RHS.
- *Texture.*—Pubescent.
- *Strength.*—Strong and flexible.

Internode length: About 1.5 cm.

FOLIAGE

Leaf:
- *Arrangement.*—Opposite.
- *Quantity.*—Approximately 16 per branch.
- *Average length.*—3.5 cm.
- *Average width.*—1.8 cm.
- *Shape of blade.*—Elliptic.
- *Apex.*—Obtuse.
- *Base.*—Acute.
- *Margin.*—Entire.
- *Texture of top surface.*—Velvety, pubescent.
- *Texture of bottom surface.*—Velvety, pubescent.
- *Aspect.*—90° angle of attachment, flat to very slightly undulating foliage.
- *Color.*—Young foliage upper side: Green group 137B RHS. Young foliage under side: Green group 137C RHS. Mature foliage upper side: Green group 137A RHS. Mature foliage under side: Green group 137C RHS.
- *Venation.*—Type: Pinnate. Venation color upper side: Green group 137A RHS. Venation color under side: Green group 137C RHS.
- *Petiole.*—Length: About 0.5 cm. Diameter: About 0.2 cm. Color: Green group 137A RHS. Texture: Velvety.

FLOWER

Natural flowering season: Spring, Summer & Autumn.
Days to flowering from rooted cutting: About 30 days.
Inflorescence and flower type and habit: Axillary, single flower, salverform shape, erect, outwardly facing habit.
Rate of flower opening: 2 to 3 days from bud to fully opened flower.
Flower longevity on plant: 3 to 6 days.
Approximate quantity of flowers per plant: About 70.
Persistent or self-cleaning: Self-Cleaning.
Bud:
- *Shape.*—Tubular.
- *Length.*—About 3.5 cm.
- *Diameter.*—About 0.5 cm.
- *Color.*—Purple group N77A RHS.

Flower size:
- *Diameter.*—About 3.5 cm.
- *Flower tube length.*—About 3.0 cm.
- *Flower tube diameter at distal end.*—0.8 cm.
- *Flower tube diameter at proximal end.*—0.2 cm.

Petals:

*Length from throat.*—About 1.5 cm.

*Width.*—About 2.0 cm.

*Quantity.*—5.

*Texture.*—Velvety both upper and lower surfaces.

*Apex.*—Blunt.

*Margin.*—Entire.

Color: Background color: When opening: Upper surface: Violet-blue group N92A RHS. Lower surface: Purple group 79A RHS. Fully opened: Upper surface: Violet-blue group N92A RHS. Lower surface: Purple group 79A RHS. Flower throat (inside): Violet-blue group N92A RHS. Flower throat, vein: Violet-blue group N92A RHS. Flower tube (outside): Purple group N77A RHS. Flower tube, vein: Yellow-green group 154A RHS. Fading: Petals fading to: Violet-blue group N92C RHS.

Description of the flower striping coloration: The flowers have five Greenish-Yellow stripes. Green-Yellow group 1 B RHS. Stripes width is usually about 6-8 mm, however, some flowers on the same plant may have wider stripes, of about 10-13 mm. Other flowers on the same plant may show less pronunciation of the Yellow stripes, as five shorter triangles around the margins, or only five Yellow dots around the margins.

Calyx/sepals:

*Quantity per flower.*—5.

*Shape.*—Linear.

*Length.*—About 1.3 cm. Corolla tube length: About 0.8 cm.

*Width.*—About 0.2 cm.

*Apex.*—Rounded.

*Base.*—Cuneate.

*Margin.*—Entire.

*Texture.*—Velvety both upper and lower surfaces.

*Color.*—Upper Surface: Green group 137B RHS. Lower Surface: Green group 137C RHS.

Peduncle:

*Length.*—About 2.0 cm.

*Diameter.*—About 0.1 cm.

*Color.*—Green group 137B RHS.

*Orientation.*—45°.

Fragrance: None.

REPRODUCTIVE ORGANS

Stamens:

*Number.*—5.

*Filament length.*—About 2.0 cm.

Anthers:

*Shape.*—Rounded.

*Length.*—About 0.1 cm.

*Color.*—Blue-green group 122B RHS.

Pollen:

*Color.*—Yellow-green group 154C RHS.

*Quantity.*—Abundant.

Pistil:

*Number.*—1.

*Length.*—About 2.2 cm.

*Style.*—Length: About 2.5 cm. Color: Yellow-green group 154C RHS.

*Stigma.*—Shape: Rounded. Color: Yellow-green group 146B RHS. Ovary Color: Yellow-green group N144C RHS.

OTHER CHARACTERISTICS

Seeds and fruits: About 60 near grey-brown N199B, rounded seeds of about 0.5 mm diameter, per one near Brown 200B conical capsule.

Disease/pest resistance: Neither resistance nor susceptibility to the normal diseases and pest of *Petunia* have been observed. Typical well known diseases include: *Botrytis cineria, Fusarium, Pythium, Phytophthora,* and *Rhizoctonia* species. Typical well known pests include: Leaf miners, spider mites, thrips and possibly caterpillars.

Temperature tolerance: From 5° to 40° C.

What is claimed is:

1. A new and distinct cultivar of *Petunia* plant named 'DLITT299' as herein illustrated and described.

* * * * *